(12) United States Patent
Taguchi

(10) Patent No.: US 11,172,894 B2
(45) Date of Patent: Nov. 16, 2021

(54) MEDICAL PROCESSING APPARATUS, X-RAY DIAGNOSIS SYSTEM, AND MEDICAL PROCESSING METHOD

(71) Applicant: CANON MEDICAL SYSTEMS CORPORATION, Otawara (JP)

(72) Inventor: Hiroki Taguchi, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 16/728,146

(22) Filed: Dec. 27, 2019

(65) Prior Publication Data

US 2020/0205751 A1    Jul. 2, 2020

(30) Foreign Application Priority Data

Dec. 27, 2018   (JP) .............................. JP2018-244900

(51) Int. Cl.
*A61B 6/03* (2006.01)
*A61B 6/00* (2006.01)

(52) U.S. Cl.
CPC ............ *A61B 6/032* (2013.01); *A61B 6/4208* (2013.01); *A61B 6/4452* (2013.01); *A61B 6/5205* (2013.01)

(58) Field of Classification Search
CPC ..... A61B 6/032; A61B 6/4208; A61B 6/4452; A61B 6/5205; A61B 6/482
See application file for complete search history.

(56) References Cited

U.S. PATENT DOCUMENTS

| | | | |
|---|---|---|---|
| 9,271,688 B2* | 3/2016 | Das ....................... | A61B 6/481 |
| 2007/0217570 A1* | 9/2007 | Grasruck ............... | A61B 6/405 |
| | | | 378/53 |
| 2009/0304249 A1* | 12/2009 | Wu ....................... | A61B 6/405 |
| | | | 382/131 |
| 2013/0182821 A1* | 7/2013 | Tsuyuki ................. | A61B 6/482 |
| | | | 378/16 |
| 2014/0050378 A1* | 2/2014 | Sengupta ............. | G01N 23/046 |
| | | | 382/131 |

(Continued)

FOREIGN PATENT DOCUMENTS

| | | |
|---|---|---|
| JP | 2011-024773 A | 2/2011 |
| WO | WO 2015/024025 A1 | 2/2015 |

OTHER PUBLICATIONS

Extended European Search Report dated Jun. 4, 2020 in European Patent Application No. 19219794.5, citing documents AO and AX therein, 8 pages.

(Continued)

*Primary Examiner* — Marcus H Taningco
(74) *Attorney, Agent, or Firm* — Oblon, McClelland, Maier & Neustadt, L.L.P.

(57) ABSTRACT

A medical processing apparatus includes processing circuitry. Based on a first number of X-ray datasets that correspond to the first number of energies and that are acquired by scanning a subject with X-rays, the processing circuitry generates a second number of virtual monochromatic X-ray datasets, which is a number larger than the first number. Based on the second number of virtual monochromatic X-ray datasets, the processing circuitry estimates quantities of the second number of reference materials mixed or a mixing ratio between the second number of reference materials for each of multiple positions in the subject.

11 Claims, 4 Drawing Sheets

(56) References Cited

U.S. PATENT DOCUMENTS

| | | | | |
|---|---|---|---|---|
| 2014/0276021 A1* | 9/2014 | Yeh | ............... | A61B 6/481 |
| | | | | 600/426 |
| 2015/0348292 A1* | 12/2015 | Taguchi | ............... | A61B 6/032 |
| | | | | 382/131 |
| 2016/0193366 A1* | 7/2016 | Yeh | ............... | A61K 49/04 |
| | | | | 424/9.4 |
| 2017/0278278 A1* | 9/2017 | Brown | ............... | G06T 11/003 |
| 2018/0263576 A1* | 9/2018 | Konno | ............... | G06T 11/003 |
| 2019/0069865 A1* | 3/2019 | Goshen | ............... | A61B 6/032 |
| 2019/0313991 A1* | 10/2019 | Proksa | ............... | A61B 6/5211 |

OTHER PUBLICATIONS

Yu, L., et al., "Pre-reconstruction three-material decomposition in dual-energy CT", Proceedings of SPIE, vol. 7258, Feb. 26, 2009, XP055098595, pp. 72583V-1 ~ 72583V-8.

\* cited by examiner

MEDICAL PROCESSING APPARATUS, X-RAY DIAGNOSIS SYSTEM, AND MEDICAL PROCESSING METHOD

CROSS-REFERENCE TO RELATED APPLICATIONS

This application is based upon and claims the benefit of priority from Japanese Patent Application No. 2018-244900, filed on Dec. 27, 2018; the entire contents of which are incorporated herein by reference.

FIELD

Embodiments descried herein relate generally to a medical processing apparatus, an X-ray diagnosis system and a medical processing method.

BACKGROUND

There has been a technique for X-ray computed tomography (CT) apparatuses to acquire images by performing imaging using different multiple types of tube voltages. For example, for dual-energy (DE) collection using different two types of tube voltages, there is a known technique of separating two sets of projection data obtained from different two tube voltages into sets of projection data of pre-set two reference substances (line integral data) and reconstructing images (reference substance images) based on the abundance ratio between the reference substances respectively from the separated two sets of data. The technique makes it possible to acquire various images, such as virtual monochromatic X-ray images, density images and effective atomic number images, by perform weight calculation processing using the two reference substance images.

DETAILED DESCRIPTION

According to an embodiment, a medical processing apparatus includes processing circuitry. The processing circuitry is configured to generate, based on a first number of X-ray datasets that correspond to the first number of energies and that are acquired by scanning a subject with X-rays, a second number of virtual monochromatic X-ray datasets, the second number being larger than the first number. The processing circuitry is configured to estimate, based on the second number of virtual monochromatic X-ray datasets, quantities of the second number of reference materials mixed or a mixing ratio between the second number of reference materials for each of multiple positions in the subject.

With reference to the accompanying drawings, embodiments of a medical processing apparatus, an X-ray diagnosis system and a medical processing method will be described in detail below. The medical processing apparatus, the X-ray diagnosis system and the medical processing method according to the present application according to the present application are not limited by the embodiments described below.

First Embodiment

First of all, a first embodiment will be described. In the first embodiment, an X-ray diagnosis system including the medical processing apparatus of the present application will be exemplified and described. In the first embodiment, an X-ray CT system is exemplified and described as the X-ray diagnosis system.

Figure 1:
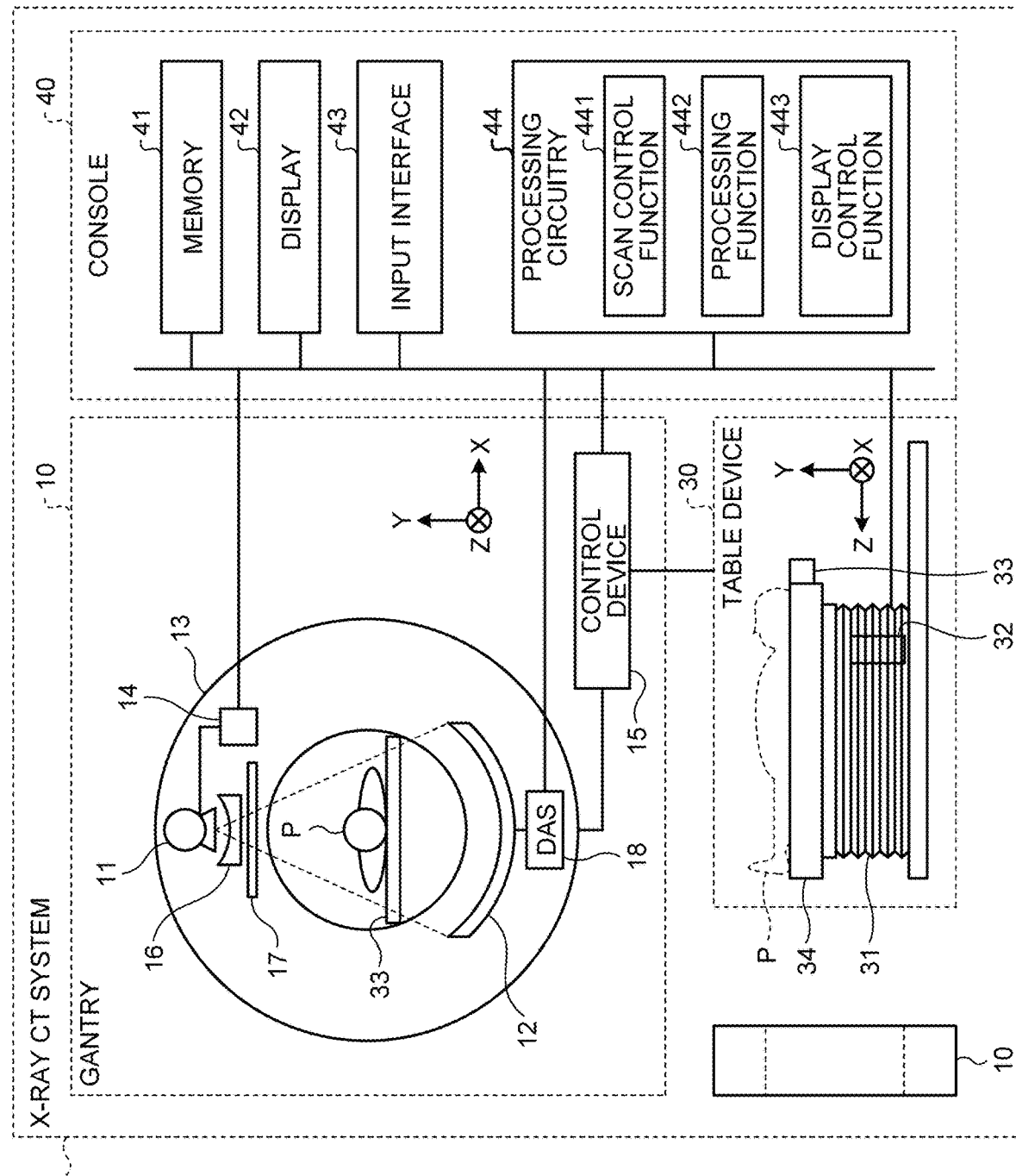
FIG. 1 is a block diagram illustrating an exemplary configuration of an X-ray CT system according to a first embodiment.

FIG. 1 is a diagram illustrating an exemplary configuration of an X-ray CT system 1 according to the first embodiment. As illustrated in FIG. 1, the X-ray CT system 1 according to the first embodiment includes a gantry 10, a table 30, and a console 40.

Figure 2:
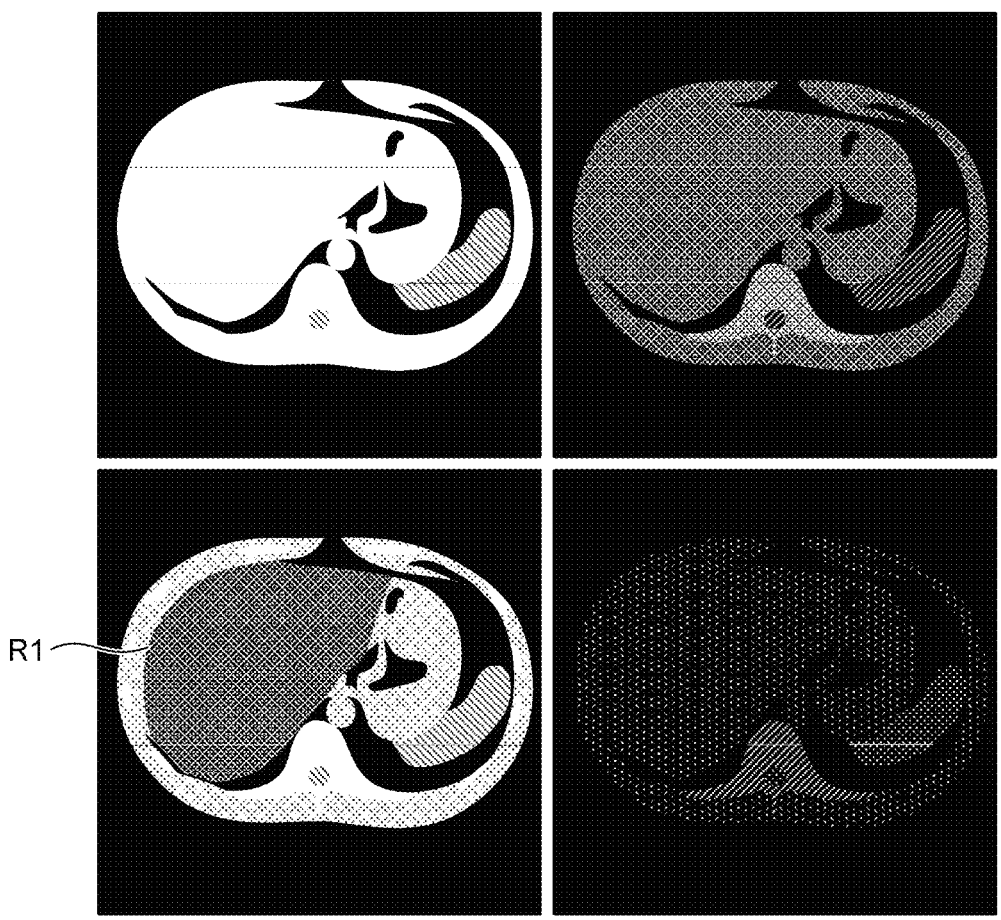
FIG. 2 is a diagram illustrating an exemplary display of display information that is made by a display control function according to the first embodiment.

In FIG. 2, a rotational axis of a rotation frame 13 being not tilted or a longitudinal direction of a table top 33 of the table 30 serves as a Z-axis direction. An axial direction that is orthogonal to the Z-axis direction and that is parallel to a floor surface serves as an X-axis direction. An axial direction that is orthogonal to the Z-axis direction and that is orthogonal to the floor surface serves as a Y-axis direction. FIG. 1 depicts the gantry 10 from multiple directions for explanation and illustrates the case where the X-ray CT system 1 includes the single gantry 1.

The gantry 10 includes an X-ray tube 11, an X-ray detector 12, the rotation frame 13, an X-ray high voltage device 14, a control device 15, a wedge 16, a collimator 17, and a data acquisition system (DAS) 18.

The X-ray tube 11 is a vacuum tube including a negative electrode (filament) that generates thermoelectrons and a positive electrode (target) that generates X-rays in response to collision of thermoelectrons. Application of a high voltage from the X-ray high voltage device 14 causes the X-ray tube 11 to emit thermoelectrons from the negative electrode to the positive electrode, thereby generating X-rays to be applied to the subject P. For example, the X-ray tube 11 is a rotation positive electrode X-ray tube that causes X-rays by applying thermoelectrons to the rotating positive electrode.

The X-ray detector 12 includes a plurality of detection elements that detect X-rays. Each of the detection elements of the X-ray detector 12 detects X-rays having been emitted from the X-ray tube 11 and having passed through a subject P and outputs a signal corresponding to the quantity of detected X-rays to the DAS 18. The X-ray detector 12, for example, includes a plurality of detection element arrays where a plurality of detection elements are arrayed in a channel direction along a single arc about a focal point of the X-ray tube 11. The X-ray detector 12, for example, has a configuration in which a plurality of detection element arrays each including a plurality of detection elements that are arrayed in the channel direction are arranged in an array direction (slice direction or row direction).

For example, the X-ray detector 12 is an indirect conversion detector including a grid, a scintillator array, and a sensor array. The scintillator array includes a plurality of scintillators. The scintillator includes a scintillator crystal that outputs light of a quantity of photons corresponding to the quantity of incident X-rays. The grid is arranged on a surface of the scintillator array on the side of incidence of X-rays and includes an X-ray shield that absorbs scattering X-rays. The gird can be also referred to as a collimator (a primary collimator or a secondary collimator). The optical sensor array has a function of conversion into an electric signal corresponding to the amount of light from the scintillator and, for example, includes an optical sensor, such as a photodiode. For example, the X-ray detector 12 is an energy integration detector. For example, the X-ray detector 12 may be a direct conversion detector including a semiconductor element that converts incident X-rays into an electric signal.

The rotation frame 13 is an annular frame that supports the X-ray tube 11 and the X-ray detector 12 such that the X-ray tube 11 and the X-ray detector 12 are opposed to each other and that rotates the X-ray tube 11 and the X-ray detector 12 using the control device 15. For example, the rotation frame 13 is a cast made of aluminum. The rotation frame 13 may further support, in addition to the X-ray tube 11 and the X-ray detector 12, the X-ray high voltage device 14, the wedge 16, the collimator 17, and the DAS 18. The rotation frame 13 may further support various structures not illustrated in FIG. 1.

The X-ray high voltage device 14 has electric circuits, such as a transformer and a rectifier, and includes a high-voltage generation device that generates a high voltage to be applied to the X-ray tube 11 and an X-ray control device that controls an output voltage corresponding to the X-rays generated by the X-ray tube 11. The high-voltage generation device may employ a transformer system or an inverter system. The X-ray high voltage device 14 may be arranged on the rotation frame 13 or may be arranged on a fixed frame (not illustrated in the drawings).

The control device 15 includes a processing circuit including a central processing unit (CPU) and a drive mechanism, such as a motor and an actuator. In response to reception of input signals from an input interface 43, the control device 15 controls operations of the gantry 10 and the table 30. For example, the control device 15 controls rotation of the rotation frame 13, tilt of the gantry 10, and operations of the table 30 and the table top 33. For example, the control device 15 causes the rotation frame 13 to rotate about an axis parallel with the X-axis direction according to a tilt angle information that is input. The control device 15 may be arranged in the gantry 10 or may be arranged in the console 40.

The wedge 16 is a filter for adjusting the quantity of X-rays that are emitted from the X-ray tube 11. Specifically, the wedge 16 is a filter that transmits and attenuates the X-rays emitted from the X-ray tube 11 such that X-rays that are emitted from the X-ray tube 11 to the subject P have a predetermined distribution. For example, the wedge 16 is a wedge filter or a bow-tie filter obtained by processing aluminum, or the like, such that the filter has a given target angle and a given thickness.

The collimator 17 is a lead plat, or the like, for narrowing the area to be irradiation with X-rays having passed through the wedge 16, where a slit is formed by combining of a plurality of lead plates. The collimator 17 can be referred to as an X-ray diaphragm. FIG. 1 illustrates the case where the wedge 16 is arranged between the X-ray tube 11 and the collimator 17. Alternatively, the collimator 17 may be arranged between the X-ray tube 11 and the wedge 16. In this case, the wedge 16 transmits X-rays whose corresponding area of irradiation is restricted by the collimator 17 and thus attenuates the X-rays.

The DAS 18 collects signals of X-rays that are detected by the respective detection elements of the X-ray detector 12. For example, the DAS 18 includes an amplifier that performs amplification processing on the electric signal that is output from each of the detection elements and an A/D converter that converts the electric signal into a digital signal, thereby generating detection data. The DAS 18 is, for example, implemented by a processor.

The data that is generated by the DAS 18 is transmitted by optical communication from a transmitter that is arranged on the rotation frame and that includes a light emitting diode (LED) to a receiver that is arranged in a non-rotation part (for example, a fixed frame not illustrated in FIG. 1) in the gantry 10 and that includes a photodiode and the data is then transferred to the console 40. The non-rotation part is, for example, a fixed frame that supports the rotation frame 13 rotatably. The method of data transmission from the rotation frame 13 to the non-rotation part of the gantry 10 is not limited to optical communication and any contactless data transmission system may be employed or a contact data transmission system may be employed.

The table 30 is a device on which the subject P to be imaged is placed and that moves the subject. The table 30 includes a base 31, a table drive device 32, the table top 33 and a support frame 34. The base 31 is a casing that supports the support frame 34 movably in the vertical direction. The table drive device 32 is a drive mechanism that moves the table top 33 with the subject P placed thereon in a longitudinal direction of the table top 33 and includes a motor, an actuator, etc. The table top 33 that is provided on the top surface of the support frame 34 is a board on which the subject P is placed. The table drive device 32 may move, in addition to the table top 33, the support frame 34 in the longitudinal direction of the table top 33.

The console 40 includes a memory 41, a display 42, the input interface 43, and processing circuitry 44. The console 40 will be described as a device independent of the gantry 10; however, the gantry 10 may include the console 40 or part of the components of the console 40. In the embodiment, for example, the console 40 incorporates the function of the medical processing apparatus according to the present application.

The memory 41 is, for example, implemented using a semiconductor memory device, such as a random access memory (RAM) or a flash memory, a hard disk or an optical disk. The memory 41, for example, stores projection data and CT image data. The memory 41 stores information on an area of interest. The area of interest will be described in detail below. For example, the memory 41 stores a program for a circuit contained in the X-ray CT system 1 to implement the function. The memory 41 may be implemented using a group of servers (cloud) that is connected with the X-ray CT system 1 via a network.

The display 42 displays various types of information. For example, the display 42 displays various images that are generated by the processing circuitry 44 or displays a graphical user interface (GUI) for receiving various operations from an operator. For example, the display 42 is a liquid crystal display or a cathode ray tube (CRT) display. The display 42 may be a desktop display or may be formed of a tablet terminal that can wirelessly communicate with the main unit of the console 40.

The input interface 43 receives various input operations from the operator, converts the received input operations into electric signals, and outputs the electric signals to the processing circuitry 44. For example, the input interface 43 receives, from the operator, reconstruction conditions on reconstructing CT image data and operations of inputting image processing conditions on generating post-processing images from the CT image data.

For example, the input interface 43 is implemented using a mouse, a keyboard, a track ball, a switch, a button, a joystick, a touch pad whose operation screen is touched to perform input operations, a touch screen including a display screen and a touch pad that are integrated, a contactless input circuit using an optical sensor, a sound input circuit, or the like. The input interface 43 may be arranged in the gantry 10. The input interface 43 may be formed of a table terminal capable of wirelessly communicating with the main unit of the console 40. The input interface 43 is not limited to one including physical operational parts, such as a mouse and a keyboard. For example, examples of the input interface 43 include an electric signal processing circuit that receives an electric signal corresponding to an input operation from an external input device arranged independently of the console 40 and that outputs the electric signal to the processing circuitry 44.

The processing circuitry 44 controls operations of the whole X-ray CT system 1. For example, the processing circuitry 44 implements a scan control function 441, a processing function 442, and a display control function 443. The processing circuitry 44 is an exemplary processing circuitry.

In the X-ray CT system 1 illustrated in FIG. 1, each processing function is stored in the memory 41 in a form of a program that is executable by a computer. The processing circuitry 44 is a processor that implements the function corresponding to each program by reading the program from the memory 41 and executing the program. In other words, the processing circuitry 44 having read each program has the function corresponding to the read program.

FIG. 1 illustrates the case where each of the scan control function 441, the processing function 442 and the display control function 443 is implemented by the single processing circuitry 44; however, embodiments are not limited to this. For example, the processing circuitry 44 may be formed by combining multiple independent processors and the processors may respectively execute programs to implement the processing functions, respectively. The processing functions of the processing circuitry 44 may be appropriately distributed to multiple processing circuits or integrated in a single processing circuit.

The general configuration of the X-ray CT system 1 according to the embodiment has been described. The configuration enables the X-ray CT system 1 to, using data on multiple types of energies, discriminate reference substances larger in number than the number of types of energies. Specifically, the X-ray CT system 1 collects data of multiple types of different energies, generates virtual monochromatic X-ray images that correspond to the energies and that are larger in number than the number of types of collected data, and discriminates reference substances larger in number than the number of types of collected data.

Note that, in the embodiment, "collecting data of multiple types of different energies" includes, in addition to "imaging by dual energy" using two types of different energies (tube voltages), "imaging by multi energy" using at least three types of different energies, and energy discrimination by photon counting (PC). In "imaging by dual energy", any one of the following five imaging methods may be used.

For example, as a first method, there is "the slow kV switching system (dual rotation system)" to, after imaging using a first tube voltage with one X-ray tube, perform imaging using a second tube voltage different from the first tube voltage. For example, as a second method, there is "the rapid kV switching system (kV switching system)" to rapidly switching the tube voltage of the X-ray tube for each view during rotation (scan). In this case, the data collection device collects data in synchronization with switching of the tube voltage and collects sets of data at different tube voltages during a single scan. Furthermore, for example, as a third method, there is "the dual source system (dual tube system)" in which not a single X-ray tube but two X-ray tubes are mounted and imaging using different tube voltages is performed using the X-ray tubes. For example, as a fourth method, there is "the layered detector system" using a multilayered X-ray detector. For example, when a double-layered X-ray detector (including a shall layer detector and a deep layer detector) is used, the shallow layer detector detects low-energy X-rays and the deep layer detector detects high-energy X-rays having passed through the shallow layer detector. For example, as a fifth embodiment, there is a system in which X-rays emitted from a single X-ray tube are separated into two energies with a split filter and sets of data of the different energies are collected at a time.

Details of the processing will be described below. The case where imaging using two types of different energies is performed by executing "imaging by dual energy" using "the rapid kV switching system" to discriminate three types of reference substances will be exemplified and described below.

The scan control function 441 controls a scan based on an input operation that is received from the operator via the input interface 43. Specifically, the scan control function 441 transmits a control signal to the X-ray high voltage device 14 according to an input operation, thereby controlling the output voltage from the high-voltage generation device. The scan control function 441 transmits a control signal to the DAS 18 to control data collection performed by the DAS 18.

By executing scanning using X-rays, the scan control function 441 collects, for an area containing part of the subject, a first dataset corresponding to the first energy and a second dataset corresponding to the second energy different from the first energy. For example, the scan control function 441 controls "imaging by dual energy" using "the rapid kV switching system".

In that case, by transmitting a control signal to switch between a high voltage and a low voltage to the X-ray high voltage device 14, the scan control function 441 controls application of the high voltage and the low voltage from the X-ray high voltage device 14 to the X-ray tube 11. By transmitting a control signal to the DAS 18, the scan control function 441 causes the DAS 18 to identify which of high voltage X-ray irradiation or low voltage X-ray irradiation causes the detected detection data.

The processing function 442 generates projection data by performing pre-processing, such as logarithmic transformation, offset correction, sensitivity correction, and beam hardening correction, on the detection data that is transmitted from the DAS 18. Note that the data before the pre-processing (detection data) and the data after the pre-processing may be collectively referred to as projection data. For example, the processing function 442 generates projection data (referred to as high energy projection data below) from the detection data of the first tube voltage (for example, a high voltage). The processing function 442 generates projection data (referred to as low energy projection data below) from the detection data of the second tube voltage (for example, a low voltage). These types of projection data also may be collectively referred to as a projection dataset.

Using the projection dataset containing the two types of projection data, the processing function 442 separates the predetermined two reference substances (water, iodine, calcium, hydroxyapatite, fat, or gadolinium) that are present in an area to be imaged. Specifically, the processing function 442 calculates, for each of the two types of projection data, a distribution of linear attenuation coefficient and calculates, for each position (each pixel) of the linear attenuation coefficient distribution, quantities of the mixed two reference substances and a mixing ratio between the two reference substances at each position by solving a simultaneous equation based on Equation (1) below. Equation (1) exemplifies the case where iodine and water are used as the reference substances.

$$\mu(E) = \mu_{Iodine}(E) \cdot c_{Iodine} + \mu_{Water}(E) \cdot c_{Water} \qquad (1)$$

In Equation (1), "$\mu(E)$" denotes a linear attenuation coefficient of each position, "$\mu_{iodine}(E)$" denotes a linear attenuation coefficient of iodine, "$\mu_{Water}(E)$" denotes a linear attenuation coefficient of water, "$c_{Iodine}$" denotes a quantity of mixed iodine, and "$c_{Water}$" denotes a quantity of mixed water. As described above, the first embodiment illustrates the case where "$\mu$" of each substance is expressed by a linear attenuation coefficient and "c" is expressed by a mixed quantity; however, embodiments are not limited thereto. For example, the density of a substance may be incorporated in "c" to express "$\mu$" of each substance by a mass attenuation coefficient or "c" may be expressed by a density. In other words, "$\mu$: linear attenuation coefficient" and "c: mixed quantity" may be appropriately replaced with "p: mass attenuation coefficient" and "c: density".

The processing function 442 calculates quantities of mixed iodine and water and a mixing ratio between iodine and water according to a simultaneous equation using two equations obtained by applying a linear attenuation coefficient of high-energy projection data and a linear attenuation coefficient of low-energy projection data to Equation (1) expressing a given substance by the two reference substances (iodine and water).

In other words, the processing function 442 creates, for each position (pixel), two equations of "$\mu(\text{high energy}) = \mu_{Iodine}(\text{high energy}) \cdot c_{Iodine} + \mu_{Water}(\text{high energy}) \cdot c_{Water}$" and "$\mu(\text{low energy}) = \mu_{Iodine}(\text{low energy}) \cdot c_{Iodine} + \mu_{Water}(\text{low energy}) \cdot c_{Water}$" and solves the equations to calculate "$c_{Iodine}$" and "$c_{Water}$" at the position. The linear attenuation coefficient each reference substance per energy is known.

As described above, the processing function 442 calculates the quantities of the mixed substances at each position using Equation (1). The processing function 442 generates two types of projection datasets corresponding to the respective two reference substances based on the quantities of the mixed two reference substances at each position. For example, the processing function 442 calculates quantities of mixed iodine and mixed water from the high-energy projection data and the low-energy projection data as described above and generates sets of projection data corresponding respectively to iodine and water. The projection datasets that are generated by the processing function 442 are stored in the memory 41.

The processing function 442 generates various images from the projection data sets that are stored in the memory 41 and stores the generated images in the memory 41. For example, the processing function 442 reconstructs CT image data by reconstructing the projection data by various reconstruction methods (for example, a back projection method, such as filtered back projection, and successive approximation) and stores the reconstructed CT image data in the memory 41. The processing function 442 generates CT images, such as MPR images, from the CT image data by performing various types of image processing and stores the generated CT images in the memory 41.

For example, the processing function 442 reads the projection datasets on the reference substances that are stored in the memory 41 and reconstructs the reference substance image data (reference-substance-enhanced image data). In an example, the processing function 442 reconstructs reference substance image data of water components based on the projection data in which the water components are enhanced and reconstructs reference substance image data on iodine components based on the projection data in which iodine components are enhanced. The processing function 442 executes image processing on each of the reference substance image data on the water components and the reference substance image data on the iodine components, thereby generating a reference substance image of the water components and a reference substance image of the iodine components. By preforming weight calculation processing based on the mixing ratio of each reference substance using the two sets of reference substance image data, the processing function 442 is able to generate various images, such as a virtual monochromatic X-ray image, a density image, and an effective atom number image corresponding to a given energy.

For example, the processing function 442 reads the high-energy projection data and the low-energy projection data that are stored in the memory 41 and reconstructs sets of CT image data from the respective sets of projection data. The processing function 442 is also capable of generating a multicolor X-ray image corresponding to the high energy and a multicolor X-ray image corresponding to the low energy from the sets of CT image data.

Using these sets of data, the processing function 442 according to the embodiment discriminates the reference substances larger in number than the number of types of energies. Specifically, based on a first number of X-ray datasets corresponding to the first number of energies that are obtained by scanning the subject with X-rays, the processing function 442 generates a larger second number of virtual monochromatic X-ray datasets than the first number and, based on the second number of virtual monochromatic X-ray datasets, the processing function 442 estimates quantities of the second number of reference substances mixed or a mixing ratio between the second number of reference substances for each of multiple positions in the subject.

More specifically, based on the first number of X-ray datasets, the processing function 442 estimates, for each of the multiple positions in the subject, quantities of the first number of reference substances mixed or the mixing ratio between the first number of reference substances, thereby generating the second number of virtual monochromatic X-ray datasets. Based on the values each representing absorption of X-rays at each position in each of the second number of virtual monochromatic X-ray datasets and the values each representing absorption of X-rays by each of the second number of reference substances, the processing function 442 then estimates quantities of the second number of reference substances mixed and a mixing ratio between the second number of reference substances. For example, the processing function 442 estimates the quantities of the second number of reference substances mixed and the mixing ratio between the second number of reference substances according to a simultaneous equation representing the values each representing absorption of X-rays at each position in each of the second number of virtual monochromatic X-ray datasets by the values each representing absorption of X-rays by each of the second number of reference substances and the mixing quantities or the densities.

For example, using the calculated quantities of the mixed reference substances at each position, the processing function 442 calculates each linear attenuation coefficient of virtual monochromatic X-rays at each position. The processing function 442 calculates the same number of virtual monochromatic X-ray linear attenuation coefficients as that of the reference substances to be discriminated. For example, to discriminate three reference substances, the processing function 442 calculates linear attenuation coefficients of the three types of energies for each position according to Equation (2) below using the quantities of mixed iodine and water that are calculated according to Equation (1).

$$\left.\begin{array}{l}\mu(E_1) = \mu_{Iodine}(E_1) \cdot c_{Iodine} + \mu_{Water}(E_1) \cdot c_{Water} \\ \mu(E_2) = \mu_{Iodine}(E_2) \cdot c_{Iodine} + \mu_{Water}(E_2) \cdot c_{Water} \\ \mu(E_3) = \mu_{Iodine}(E_3) \cdot c_{Iodine} + \mu_{Water}(E_3) \cdot c_{Water}\end{array}\right\} \quad (2)$$

In other words, as represented by Equation (2), the processing function 442 calculates a linear attenuation coefficient "$\mu(E_1)$" of a first monochromatic X-ray energy "$E_1$" using a linear attenuation coefficient "$\mu_{Iodine}(E_1)$" of iodine of the first monochromatic X-ray energy "$E_1$", a linear attenuation coefficient "$\mu_{Water}(E_1)$" of water of the first monochromatic X-ray energy "$E_1$", and "$c_{Iodine}$" and "$c_{Water}$" that are calculated according to Equation (1).

As represented by Equation (2), the processing function 442 calculates a linear attenuation coefficient "$\mu(E_2)$" of a second monochromatic X-ray energy "$E_2$" using a linear attenuation coefficient "$\mu_{Iodine}(E_2)$" of iodine of the second monochromatic X-ray energy "$E_2$", a linear attenuation coefficient "$\mu_{Water}(E_2)$" of water of the second monochromatic X-ray energy "$E_2$", and "$c_{Iodine}$" and "$c_{Water}$" that are calculated according to Equation (1).

As represented by Equation (2), the processing function 442 calculates a linear attenuation coefficient "$\mu(E_3)$" of a third monochromatic X-ray energy "$E_3$" using a linear attenuation coefficient "$\mu_{Iodine}(E_3)$" of iodine of the third monochromatic X-ray energy "$E_3$", a linear attenuation coefficient "$\mu_{Water}(E_3)$" of water of the third monochromatic X-ray energy "$E_3$", and "$c_{Iodine}$" and "$c_{Water}$" that are calculated according to Equation (1).

The processing function 442 is also able to generate a virtual monochromatic X-ray image by performing CT value conversion on the liner attenuation coefficients of virtual monochromatic X-rays represented by Equation (2). The linear attenuation coefficient of each reference substance corresponding to each monochromatic X-ray energy is known.

The processing function 442 calculates, for each position, each of "$\mu(E_1)$", "$\mu(E_2)$" and "$\mu(E_3)$" described above. The processing function 442 solves the simultaneous equation based on Equation (3) below expressing the given substance by three reference substances, thereby calculating quantities of the mixed three reference substances and a mixing ratio between the three reference substances at each position. Equation (3) below exemplifies the case where, in addition to iodine and water, a new substance is used as a reference substance.

$$\mu(E) = \mu_{Iodine}(E) \cdot c'_{Iodine} + \mu_{Water}(E) \cdot c'_{Water} + \mu_{New}(E) \cdot c'_{New} \quad (3)$$

In Equation (3), "$\mu(E)$" denotes a linear attenuation coefficient at each position, "$\mu_{Iodine}(E)$" denotes a linear attenuation coefficient of iodine, "$\mu_{Water}(E)$" denotes a linear attenuation coefficient of water, "$\mu_{New}(E)$" denotes a linear attenuation coefficient of the new reference substance, "$c'_{Iodine}$" denotes a quantity of mixed iodine, "$c'_{Water}$" denotes a quantity of mixed water, and "$c'_{New}$" denotes a quantity of the mixed new reference substance.

The processing function 442 calculates the quantities of mixed iodine, water, and new reference substance according to a simultaneous equation (Equation (4) below) using three equations obtained by applying the liner attenuation coefficients "$\mu(E_1)$", "$\mu(E_2)$" and "$\mu(E_3)$" to Equation (3) that expresses the given substance by the three reference substances (iodine, water and the new substance).

$$\left.\begin{array}{l}\mu(E_1) = \mu_{Iodine}(E_1) \cdot c'_{Iodine} + \mu_{Water}(E_1) \cdot c'_{Water} + \mu_{New}(E_1) \cdot c'_{New} \\ \mu(E_2) = \mu_{Iodine}(E_2) \cdot c'_{Iodine} + \mu_{Water}(E_2) \cdot c'_{Water} + \mu_{New}(E_2) \cdot c'_{New} \\ \mu(E_3) = \mu_{Iodine}(E_3) \cdot c'_{Iodine} + \mu_{Water}(E_3) \cdot c'_{Water} + \mu_{New}(E_3) \cdot c'_{New}\end{array}\right\} \quad (4)$$

In other words, as represented in Equation (4), by creating the equation obtained by applying the linear attenuation coefficient "$\mu(E_1)$" corresponding to the first monochromatic X-ray energy "$E_1$" and the linear attenuation coefficient of each reference substance corresponding to the first monochromatic X-ray energy "$E_1$" to Equation (3), the equation obtained by applying the linear attenuation coefficient "$\mu(E_2)$" corresponding to the second monochromatic X-ray energy "$E_2$" and the linear attenuation coefficient of each reference substance corresponding to the second monochromatic X-ray energy "$E_2$" to Equation (3), and the equation obtained by applying the linear attenuation coefficient "$\mu(E_3)$" corresponding to the third monochromatic X-ray energy "$E_3$" and the linear attenuation coefficient of each reference substance corresponding to the third monochromatic X-ray energy "$E_3$" to Equation (3) and then solving the equations, the processing function 442 calculates "$c'_{Iodine}$", "$c'_{Water}$" and "$c'_{New}$" at each position.

As described above, the processing function 442 is able to discriminate the reference substances larger in number than the number of types of energies by calculating the quantities of the respective reference substance at each position. Based on the quantities of the mixed three reference substances at each position, the processing function 442 generates three types of projection datasets corresponding respectively to the three reference substances. For example, the processing function 442 calculates quantities of the mixed iodine, water and new material as described above from the high-energy projection data and the low-energy projection data and generates sets of projection data corresponding respectively to iodine, water and the new reference substance.

The processing function 442 further reconstructs the reference substance image data of iodine components based on the projection data in which the iodine components are enhanced, reconstructs the reference substance image data of water components based on the projection data in which the water components are enhanced, and reconstructs the reference substance image data of components of the new reference substance based on the projection data in which the new reference substance components are enhanced. The processing function 442 further executes image processing on each of the reference substance image data of the iodine components, the reference substance image data of the water components, and the reference substance image data of the new reference substance components, thereby generating the reference substance image of the iodine components, the reference substance image of the water components, and the reference substance image of the new reference substance components. By performing weight calculation processing based on the mixing ratio of each reference substance using the three sets of reference substance image data, the processing function 442 is also able to generate various images, such as a virtual monochromatic X-ray image, a density image, and an effective atomic number image, corresponding to a given energy.

The display control function 443 causes the display 42 to display various types of display information that are generated by the processing function 442 and a GUI. For example, the display control function 443 causes the display 42 to display information containing various reference substance mages, various images, such as virtual monochromatic X-ray images and multicolor X-ray images, information representing the mixing ratio of the reference substances, etc.

As described above, using the sets of data of the multiple types of energies, the processing function 442 according to the embodiment discriminates the reference substances larger in number than the number of types of energies. An exemplary diagnosis to which the technique according to the present application is applied will be described below.

For example, the processing function 442 is able to provide data for diagnosing fatty lever by discriminating three reference substances of a contrast agent (iodine), water, and fat from the high-energy projection data and the low-energy projection data that are collected by "imaging by dual energy" on a lever.

In other words, an equation representing a liner attenuation coefficient in the case where the reference substances are iodine, water and fat is represented by Equation (5) below, where "$\mu_{fat}(E)$" denotes a linear attenuation coefficient of fat and "$c_{fat}$" denotes a quantity of mixed fat.

$$\mu(E) = \mu_{Iodine}(E) \cdot c_{Iodine} + \mu_{Water}(E) \cdot c_{Water} + \mu_{Fat}(E) \cdot c_{Fat} \quad (5)$$

As described above, the processing function 442 calculates each of liner attenuation coefficients of three types of virtual monochromatic X-ray energies for each positon. By solving a simultaneous equation based on Equation (5) expressing the given substance by iodine, water and fat, the processing function 442 calculates quantities of the mixed three reference substances and the mixture ratio of the three reference substances at each position in the lever. In other words, according to the simultaneous equation using the three equations obtained by applying the linear attenuation coefficients of the three types of virtual monochromatic X-ray energies to Equation (5), the processing function 442 calculates "$c_{Iodine}$", "$c_{Water}$" and "$c_{fat}$" at each position and thus calculates the quantities of mixed iodine, water and fat and the mixing ratio of iodine, water and fat in the lever.

For example, when the value of "$c_{fat}$" is high, there is a possibility that a diagnosis of fat liver can be made. The processing function 442 then generates reference substance images of iodine, water and fat and stores the reference substance images in the memory 41.

The display control function 443 causes the display 42 to display the mixing quantity and ratio of each reference substance and each reference substance image. FIG. 2 is a diagram illustrating an exemplary display of display information that is made by the display control function 443 according to the first embodiment.

As illustrated in FIG. 2, the display control function 443 causes the display 42 to display information containing a reference substance image of water components (upper left), a reference substance image of fat components (upper right), a reference substance image of iodine components (lower right), and a virtual monochromatic X-ray image corresponding to a given energy (lower left). For example, when the value of "$c_{fat}$" in the lever is high, the display control function 443 makes a display where a lever area is enhanced as illustrated in Area R1. Although it is not illustrated, the display control function 443 enables a display of the value of "$c_{fat}$" and the mixing ratio between iodine, water and fat. In this manner, the display control function 443 enables display of data for diagnosing fat lever.

In the above-described embodiment, the case where iodine, water and fat are used as the reference substances has been described; however, embodiments are not limited to this, and any reference substance may be used. For example, in addition to calcium, hydroxyapatite, and gadolinium mentioned above, a substance contained in a given tumor may be used as a reference substance. For example, using the substance contained in the given tumor as a reference substance may contribute to identifying the grade of the tumor and benignity or malignancy.

The above-described embodiment illustrates the case where three types of reference substances are discriminated using the sets of data collected using the two types of energies has been described. Embodiments are however not limited thereto, and at least four types of reference substances may be discriminated using sets of data collected using two types of energies. In such a case, based on quantities of the mixed two types of reference substances that are calculated from the data that is collected using the two types of energies, the processing function 442 calculates linear attenuation coefficients of at least four types of virtual monochromatic X-ray energies.

The above-described embodiment illustrates the case where the calculated quantities of the mixed reference substances are directly used has been described. Embodiments are however not limited thereto and, for example, the calculated quantities of the multiple types of reference substances may be corrected using quantities of the mixed reference substances based on data obtained by performing energy discrimination with a photon counting detector.

In that case, the processing function 442 generates output data by inputting quantities of a second number of reference substances mixed or a mixing ratio between the second number of reference substances that is estimated based on a first number of X-ray datasets corresponding to the first number of energies to a trained model that generates output data that apparently represents the quantities of the second number of reference substances mixed or the mixing ratio of the second number of reference substances that is obtained from the second number of X-ray datasets corresponding to the second number of energies that are discriminated using a photon counting X-ray detector based on the quantities of the second number of reference substances mixed or the mixing ratio of the second number of reference substances that is estimated based on the first number of X-ray datasets corresponding to the first number of energies.

For example, as described above, a trained model is stored in the memory 41, which is a rained model obtained by by using, as training data, quantities of three types of reference substances mixed that are estimated based on projection datasets of two types of energies as described above and quantities of the three types of reference substances mixed that are estimated based on projection datasets that are discriminated according to the three types of energies by the photon counting X-ray detector using a single type of energy and by learning the relationship thereof.

By inputting the quantities of the three types of reference substances mixed that are newly estimated based on the projection datasets of the two types of energies to the trained model that is stored in the memory 41, the processing function 442 performs correction to values apparently representing the quantities of the three types of reference substances mixed that are estimated based on the projection datasets that are discriminated according to the three types of energies by the photon counting X-ray detector.

The photon counting X-ray detector is able to acquire sets of projection data of three types of energies actually and thus it is assumed that the quantities of the three types of reference substances that are calculated based on the data have higher accuracy than that of values obtained by calculation. Thus, use of the above-described trained model enables the processing function 442 to calculate mixed quantities or a mixing ratio whose accuracy is higher than that of calculated quantities of reference substances mixed or a calculated mixing ratio between the reference substances.

The above-described embodiment illustrates the case where the quantity of each reference substance mixed is calculated from the distribution of linear attenuation coefficients (image data) and, from the calculated mixed quantities, each distribution of liner attenuation coefficients of a virtual monochromatic X-ray energy is calculated. Embodiments are however not limited thereto, and a quantity of each reference substance mixed may be calculated using projection data and projection data of a virtual monochromatic X-ray energy may be generated from the calculated mixed quantity.

In such a case, Equations (1) to (5) of linear attenuation coefficients described above are transformed into equations containing a length of each reference substance. Using the transformed equations, the processing function 442 calculates a quantity of each reference substance mixed and a mixing ratio of each reference substance.

Figure 3:
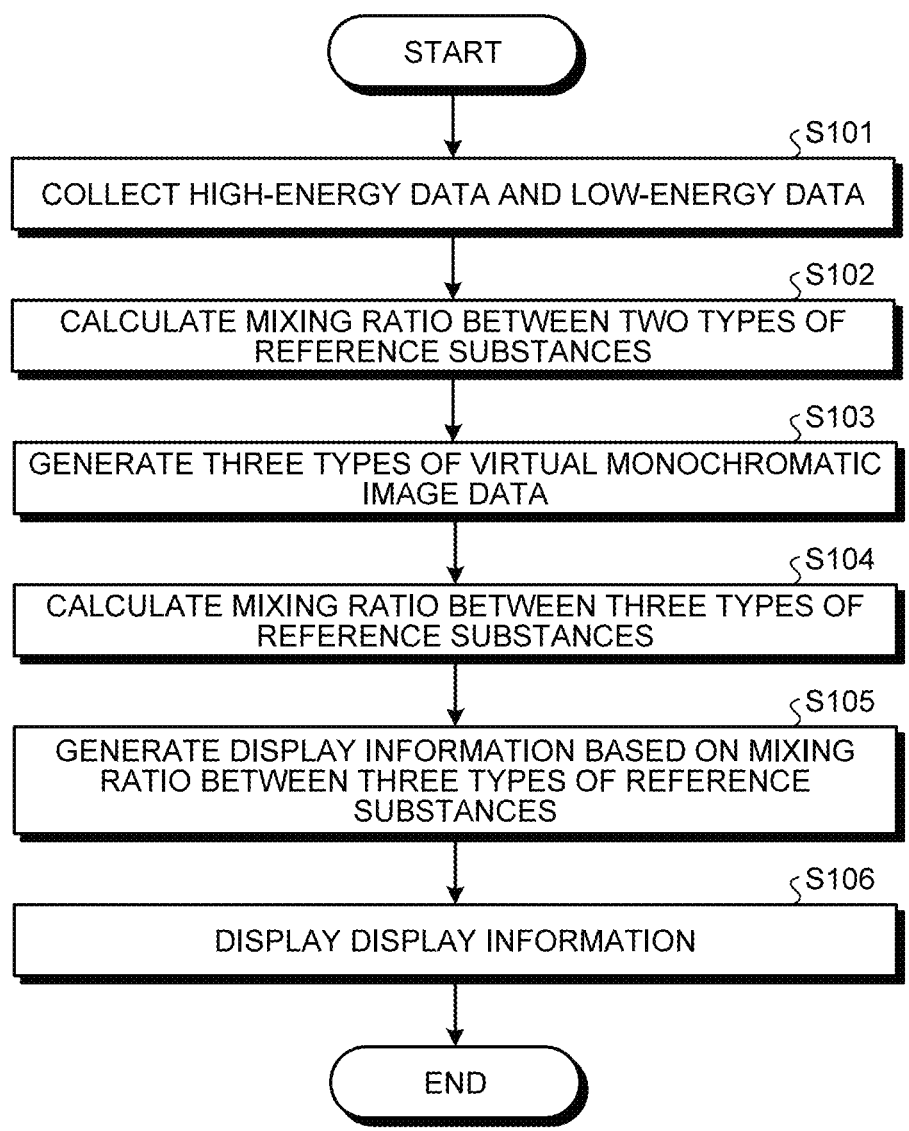
FIG. 3 is a flowchart for illustrating a flow of a process performed by the X-ray CT system according to the first embodiment.

An exemplary procedure of a process performed by the X-ray CT system 1 will be described using FIG. 3. FIG. 3 is a flowchart for illustrating the flow of the process performed by the X-ray CT system 1 according to the first embodiment. FIG. 3 illustrates the case where a ratio between the three types of reference substances is calculated using two types of data of high-energy data and low-energy data.

Step S101 is a step that is implemented by the processing circuitry 44 by reading and executing a program corresponding to the scan control function 441. Steps S102 to S105 are steps that are implemented by the processing circuitry 44 by reading and executing a program corresponding to the processing function 442. Step S106 is a step that is implemented by the processing circuitry 44 by reading and executing a program corresponding to the display control function 443.

First of all, the processing circuitry 44 collects high-energy data and low-energy data (step S101). The processing circuitry 44 then calculates a mixing ratio between two types of reference substances (step S102) and generates three types of virtual monochromatic X-ray image data (step S103).

Thereafter, based on the three types of virtual monochromatic X-ray image data, the processing circuitry 44 calculates a mixing ratio between three types of reference substances (step S104) and generates display information based on the mixing ratio between the three types of reference substances (step S105). The processing circuitry 44 then causes the display 42 to display the generated display information (step S106).

As described above, according to the first embodiment, based on a first number of X-ray datasets that correspond to the first number of energies and that are obtained by scanning a subject with X-rays, the processing function 442 generates a second number of virtual monochromatic X-ray datasets, which is a number larger than the first number, and, based on the second number of virtual monochromatic X-ray datasets, estimates quantities of the second number of reference substances mixed or a mixing ratio between the second number of reference substances for each of multiple positions in the subject. Accordingly, the X-ray CT system 1 according to the first embodiment enables discrimination of reference substances larger in number than the number of types of energies using data of multiple types of energies.

For example, in normal "imaging by dual energy", two types of reference substances are calculate by collecting data of two types of energies and, to discriminate more than two types of reference substances, it is required to perform imaging using the corresponding number of energies.

A current X-ray CT system, however, performs imaging using successive X-rays and thus, even when the X-ray CT system performs imaging using at least three types of energies, spectra overlap and the energies cannot be differentiated and therefore it is difficult to perform imaging using at least three types of energies. The "rapid kV switching system" has difficulty in switching between at least three types of energies at high speed and, even if the energy is switched, the data is sparse and this makes it difficult to perform imaging using at least three types of energies. Mounting at least three X-ray tubes enables imaging using at least three types of energies; however, this increases the size of the device thus it is not practical.

The X-ray CT system 1 according to the first embodiment does not cause such a problem and makes it possible to, using data of multiple types of energies, discriminate reference substances larger in number than the number of types of energies.

As described above, according to the first embodiment, the processing function 442 estimates, for each of multiple positions in a subject, quantities of a first number of reference substances mixed or a mixing ratio between the first number of reference substances based on the first number of X-ray datasets, thereby generating a second number of virtual monochromatic X-ray datasets. Based on values each representing absorption of X-rays at each position in each of the second number of virtual monochromatic X-ray data sets and values each representing absorption of X-rays by each of the second number of reference substances, the processing function 442 estimates quantities of the second number of reference substances mixed or a mixing ratio between the second number of reference substances. Thus, the X-ray CT system 1 according to the first embodiment enables discrimination of reference substances larger in number than the number of types of energies by only using the virtual monochromatic X-ray data sets.

As described above, according to the first embodiment, each of the X-ray datasets and the virtual monochromatic X-ray datasets is an image dataset. Each of the X-ray datasets and the virtual monochromatic X-ray datasets is a projection dataset. Accordingly, the X-ray CT system 1 according to the first embodiment enables processing using any one of image datasets and projection datasets.

As described above, according to the first embodiment, the processing function 442 estimates the quantities of the second number of reference substances mixed and the mixing ratio between the second number of reference substances according to a simultaneous equation representing the values each representing absorption of X-rays for each position in the second number of virtual monochromatic X-ray datasets by the values each representing absorption of X-rays by each of the second number of reference substances and the mixed quantities or densities. The X-ray CT system 1 according to the first embodiment thus enables easy discrimination of reference substances larger in number than the number of types of energies.

As described above, according to the first embodiment, the X-ray datasets are obtained by detecting X-rays having transmitted through the subject with an energy integration X-ray detector. Thus, the X-ray CT system 1 according to the first embodiment is able to discriminate reference substances larger in number than the number of types of energies without performing imaging using the same number of energies as the number of reference substances to be discriminated.

As described above, according to the first embodiment, the processing function 442 generates output data by inputting quantities of a second number of reference substances mixed or a mixing ratio between the second number of reference substances that is estimated based on a first number of X-ray datasets corresponding to the first number of energies to a trained model that generates output data that apparently represents the quantities of the second number of reference substances mixed or the mixing ratio of the second number of reference substances that is obtained from the second number of X-ray datasets corresponding to the second number of energies that are discriminated using a photon counting X-ray detector based on the quantities of the second number of reference substances mixed or the mixing ratio of the second number of reference substances that is estimated based on the first number of X-ray datasets corresponding to the first number of energies. Thus, the X-ray CT system 1 according to the first embodiment is able to estimate more accurate mixed quantities and mixing ratio.

Other Embodiments

The first embodiment has been described, and various different embodiments may be carried out in addition to the above-described first embodiment.

The above-described embodiment illustrates the case where high-energy projection data and low-energy projection data that are collected by imaging by dual energy with an energy integration X-ray detector. Embodiments are however not limited thereto, and X-ray datasets that are discriminated by a photon counting X-ray detector may be used.

For example, in a photon counting X-ray detector, three types of reference substances may be discriminated using sets of projection data of two types of energies that are collected by two Bins. In the photon counting X-ray detector, increasing the number of Bins reduces the quantity of X-rays in a single Bin and thus results in a highly noisy image. In the photon counting X-ray detector, increasing the number of Bins may have a risk that the amount of data may increase and thus a delay may occur in data transmission.

Application of the technique according to the present application to data that is collected by a photon counting X-ray detector enables improvement in image quality and inhibition of occurrence of delay in data transmission.

The above-described embodiment illustrates the case where the calculated quantities of the three types of reference substances mixed are corrected using the quantities of the three types of reference substances mixed based on the sets of data discriminated according to the energies by the photon counting detector. Embodiments are however not limited thereto, and quantities of three types of reference substances mixed may be acquired from quantities of two types of reference substances that are calculated by imaging by dual energy, using quantities of three types of reference substances mixed based on sets of data that are discriminated according to the energies by the photon counting detector.

In such a case, the processing function 442 generates output data by inputting quantities of a first number of reference substances mixed or a mixing ratio between the first number of reference substances that is estimated based on the first number of X-ray datasets corresponding to the first number of energies to a trained model that generates output data that apparently represents the quantities of a second number of reference substances mixed or a mixing ratio of the second number of reference substances that is obtained from the second number of X-ray datasets corresponding to the second number of energies that are discriminated using the photon counting X-ray detector based on the quantities of the first number of reference substances mixed or the mixing ratio between the first number of reference substances that is estimated based on the first number of X-ray datasets corresponding to the first number of energies.

For example, as described above, the trained model is stored in the memory 41, which is a model obtained by using, as training data, the quantities of the two types of reference substances mixed that are calculated based on the projection datasets corresponding to the two types of energies and the quantities of the three types of reference substances mixed that are estimated based on the projection datasets discriminated according to the three types of energies by the photon counting X-ray detector using a single type of energy and by learning the relationship thereof.

By newly inputting the quantities of the two types of reference substances mixed that are calculated based on the projection datasets of the two types of energies to the trained model that is stored in the memory 41, the processing function 442 acquires values apparently representing the quantities of the three types of reference substances mixed that are estimated based on the projection datasets that are discriminated according to the three types of energies by the photon counting X-ray detector.

The above-described embodiment illustrates the case where the calculated quantities of the three types of reference substances mixed are corrected using the quantities of the three types of reference substances mixed based on the sets of data discriminated according to the energies by the photon counting detector. Embodiments are however not limited thereto, and quantities of three types of reference substances mixed may be acquired from virtual monochromatic X-ray images corresponding to three types of energies that are acquired based on projection datasets of two types of energies, using quantities of three types of reference substances mixed based on sets of data that are discriminated according to the energies by the photon counting detector.

In that case, the processing function 442 generates output data by inputting a second number of virtual monochromatic X-ray datasets that are generated based on a first number of X-ray datasets corresponding to the first number of energies to a trained model that generates output data that apparently represent quantities of the second number of reference substances mixed or a mixing ratio of the second number of reference substances that is obtained from the second number of X-ray datasets corresponding to the second number of energies that are discriminated using the photon counting X-ray detector based on the second number of virtual monochromatic X-ray datasets that are generated based on the first number of X-ray datasets corresponding to the first number of energies.

For example, a trained model is stored in the memory 41, which is the trained model obtained by using, as training data, virtual monochromatic X-ray images corresponding to three types of energies that are generated based on projection datasets of two types of energies and quantities of the three types of reference substances mixed that are estimated based on projection datasets that are discriminated according to the three types of energies by the photon counting X-ray detector using a single type of energy and by learning the relationship thereof.

By newly inputting the virtual monochromatic X-ray images corresponding to the three types of energies that are generated based on the projection datasets of the two types of energies to the trained model that is stored in the memory 41, the processing function 442 acquires values apparently representing the quantities of the three types of reference substances mixed that are estimated based on the projection datasets that are discriminated according to the three types of energies by the photon counting X-ray detector.

Figure 4:
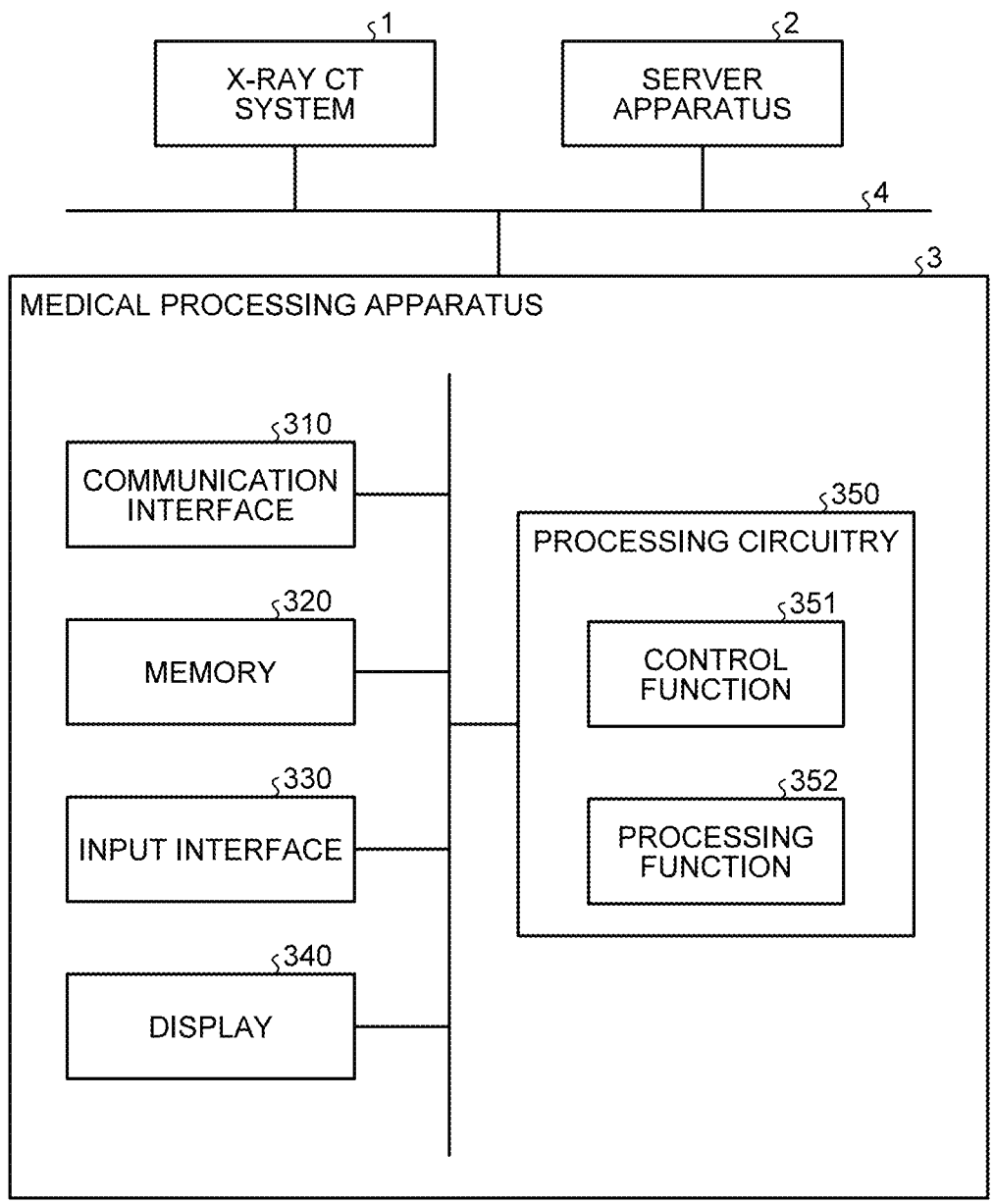
FIG. 4 is a block diagram illustrating an exemplary configuration of a medical processing apparatus according to another embodiment.

The above-described embodiment illustrates the case where the X-ray CT system 1 executes various types of processing. Embodiments however are not limited thereto and, for example, a medical processing apparatus 3 may execute various types of processing. FIG. 4 is a block diagram illustrating an exemplary configuration of the medical processing apparatus 3 according to another embodiment.

As illustrated in FIG. 4, the medical processing apparatus 3 according to another embodiment is connected to each of the X-ray CT system 1 and a server apparatus 2 via a network 4. The server apparatus 2 stores CT image data that is collected by the X-ray CT system 1. For example, the server apparatus 2 is implemented using a computer device.

As illustrated in FIG. 4, the medical processing apparatus 3 includes a communication interface 310, a memory 320, an input interface 330, a display 340, and processing circuitry 350.

The communication interface 310 is connected to the processing circuitry 350 and controls communication performed between the medical processing apparatus 3 and each system. Specifically, the communication interface 310 receives various types of information from each system and outputs the received information to the processing circuitry 350. For example, the communication interface 310 is implemented using network card, a network adapter, or a network interface controller (NIC).

The memory 320 is connected to the processing circuitry 350 and stores various types of data. For example, the memory 320 is implemented using a semiconductor memory device, such as a random access memory (RAM) or a flash memory, a hard disk, or an optical disk. For example, the memory 320 stores CT image data that is received from the X-ray CT system 1 or the image storage device 2. The memory 320 stores a program corresponding to each processing function that is executed by the processing circuitry 350.

The input interface 330 is implemented using a track ball, a switch button, a mouse, a keyboard, a touch pad whose operation screen is input to perform input operations, a touch screen including a display screen and a touch pad that are integrated, a contactless input circuit using an optical sensor, a sound input circuit, or the like.

The input interface 330 is connected to the processing circuitry 350 and converts an input operation that is received by an operator into an electric signal and outputs the electric signal to the processing circuitry 350. The input interface 330 is not limited to an interface with a physical operational part, such as a mouse or a keyboard. For example, examples of the input interface include a processing circuit that receives an electric signal corresponding to an input operation from an external input device that is arranged independently of the apparatus and outputs the electric signal to the processing circuitry 350.

The display 340 is connected to the processing circuitry 350 and displays various types of information and various types of image data that are output from the processing circuitry 350. For example, the display 340 is implemented using a liquid crystal monitor, a cathode ray tube (CRT) monitor, or a touch panel. For example, the display 340 displays a GUI for receiving instructions from the operator and various types of information.

The processing circuitry 350 controls each component of the medical processing apparatus 3 according to an input operation that is received from the operator via the input interface 330. For example, the processing circuitry 350 is implemented using a processor. In the embodiment, the processing circuitry 350 stores CT image data that is output from the communication interface 310 in the memory 320. The processing circuitry 350 reads the CT image data from the memory 320 and executes various types of processing on the CT image data or causes the display 340 to display the CT image data.

As illustrated in FIG. 4, the processing circuitry 350 implements a control function 351 and a processing function 352. The control function 351 controls the whole medical processing apparatus 3. The processing function 352 is an exemplary processor and executes the same process as that executed by the processing function 442.

The above-described embodiment illustrates the independent processes performed by the X-ray CT system 1 and the medical processing apparatus 3. Embodiments are however not limited thereto, and the X-ray CT system 1 and the medical processing apparatus 3 may cooperatively function as an X-ray CT system.

The word "processor" used in the descriptions given above refers to, for example, a central processing unit (CPU), a graphics processing unit (GPU), or a circuit, such as an application specific integrated circuit (ASIC), a programmable logic device (for example, a simple programmable logic device (SPLD), a complex programmable logic device (CPLD) or a field programmable gate array (FPGA)). The processor reads a program that is saved in a memory or a storage circuit and executes the program, thereby implementing the function.

FIG. 1 illustrates that the single memory 41 stores the programs corresponding to the respective processing functions. FIG. 4 illustrates that the single memory 320 stores a program corresponding to each processing function. Embodiments are however not limited thereto. For example, a plurality of memories 41 may be arranged in a distributed manner and the processing circuitry 44 may be configured to read the corresponding program from the individual memory 41. For example, a plurality of memories 320 may be arranged in a distributed manner and the processing circuitry 350 may be configured to read a corresponding program from the individual memory 320. Instead of saving the program in the memory 41 or the memory 320, the program may be directly incorporated in the circuit of the processor. In this case, the processor reads the program that is incorporated in the circuit and executes the program incorporated in the circuit and executes the program, thereby implementing the function.

The processing circuitry 44 and the processing circuitry 350 may implement the functions using a processor of an external device that is connected via a network. For example, the processing circuitry 44 reads a program corresponding to each function from the memory 41 and executes the program and uses an external work station or a cloud that is connected with the X-ray CT system 1 via a network as computation resources, thereby implementing each function illustrated in FIG. 1. For example, the processing circuitry 350 reads a program corresponding to each function from the memory 320 and executes the program and uses an external work station or a cloud that is connected with the medical processing apparatus 3 via a network as computation resources, thereby implementing each function illustrated in FIG. 4.

Each of the components of each of the devices according to the above-described embodiments is a functional idea and thus need not necessarily be configured physically as unillustrated in the drawings. In other words, specific modes of distribution and integration of the devices are not limited to those illustrated in the drawings, and all or part of the devices may be configured in a distributed or integrated manner functionally or physically in any unit according to various types of loads and the situation in which the devices are used. Furthermore, all or any part of the processing functions implemented by the devices may be implemented by a CPU and a program that is analyzed and executed by the CPU or may be implemented as wired logic hardware.

The processing method described in the above-described embodiments can be implemented by executing a processing program prepared in advance with a computer, such as a personal computer or a work station. The processing program can be distributed via a network, such as the Internet. The processing program may be recorded in a computer-readable medium, such as a hard disk, a flexible disk (FD), a CD-ROM, a MO or a DVD) and may be read from the recording medium by the computer and thus executed.

According to at least one of the above-described embodiments, it is possible to, using data of multiple types of energies, discriminate reference substances larger in number than the number of types of energies.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical processing apparatus comprising:
processing circuitry configured to
estimate, based on a first number of X-ray datasets that correspond to a first number of energies and that are acquired by scanning a subject with X-rays, quantities of the first number of reference materials mixed or a mixing ratio between the first number of reference materials for each of multiple positions in the subject,
generate, based on the quantities of the first number of reference materials mixed or the mixing ratio between the first number of reference materials, a second number of virtual monochromatic X-ray datasets, the second number being larger than the first number, and
estimate, based on the second number of virtual monochromatic X-ray datasets, quantities of the second number of reference materials mixed or a mixing ratio between the second number of reference materials for each of the multiple positions in the subject.

2. The medical processing apparatus according to claim 1, wherein each of the X-ray datasets and the virtual monochromatic X-ray datasets is an image dataset.

3. The medical processing apparatus according to claim 1, wherein each of the X-ray datasets and the virtual monochromatic X-ray datasets is a projection dataset.

4. The medical processing apparatus according to claim 1, wherein the processing circuitry is configured to estimate the quantities of the second number of reference materials mixed or the mixing ratio between the second number of reference materials based on values each representing absorption of X-rays at each position in each of the second number of virtual monochromatic X-ray datasets and values each representing absorption of X-rays by each of the second number of reference materials.

5. The medical processing apparatus according to claim 4, wherein the processing circuitry is configured to estimate the quantities of the second number of reference materials mixed or the mixing ratio between the second number of reference materials according to a simultaneous equation representing the values each representing absorption of X-rays at each position in each of the second number of virtual monochromatic X-ray datasets by the values each representing absorption of X-rays by each of the second number of reference materials.

6. The medical processing apparatus according to claim 1, wherein the X-ray datasets are obtained by detecting the X-rays that have transmitted through the subject using an energy integration X-ray detector.

7. The medical processing apparatus according to claim 1, wherein the X-ray datasets are obtained by detecting the X-rays that have transmitted through the subject using a photon counting X-ray detector.

8. The medical processing apparatus according to claim 1, wherein
the first number is 2, and
the second number is 3.

9. The medical processing apparatus according to claim 1, wherein the processing circuitry is configured to generate output data by inputting the quantities of the second number of reference materials mixed or the mixing ratio between the second number of reference materials that is estimated based on the first number of X-ray datasets corresponding to the first number of energies to a trained model that generates the output data that apparently represent the quantities of the second number of reference materials mixed or the mixing ratio between the second number of reference materials that is obtained from the second number of X-ray datasets corresponding to the second number of energies that are discriminated using a photon counting X-ray detector based on the quantities of the second number of reference materials mixed or the mixing ratio between the second number of reference materials that is estimated based on the first number of X-ray data sets corresponding to the first number of energies.

10. An X-ray system comprising the medical processing apparatus according to claim 1.

11. A medical processing method comprising:
estimating, based on a first number of X-ray datasets that correspond to a first number of energies and that are acquired by scanning a subject with X-rays, quantities of the first number of reference materials mixed or a mixing ratio between the first number of reference materials for each of multiple positions in the subject,
generating, based on the quantities of the first number of reference materials mixed or the mixing ratio between the first number of reference materials, a second number of virtual monochromatic X-ray datasets, the second number being larger than the first number, and
estimating, based on the second number of virtual monochromatic X-ray datasets, quantities of the second number of reference materials mixed or a mixing ratio between the second number of reference materials for each of the multiple positions in the subject.

\* \* \* \* \*